United States Patent
Tomes et al.

(10) Patent No.: US 7,928,287 B2
(45) Date of Patent: Apr. 19, 2011

(54) METHODS FOR LARGE SCALE FUNCTIONAL EVALUATION OF NUCLEOTIDE SEQUENCES IN PLANTS

(75) Inventors: Dwight T. Tomes, Van Meter, IA (US); Deping Xu, Johnston, IA (US); Haiyin Wang, Johnston, IA (US); Xiaomu Niu, Johnston, IA (US); Igor C. Oliveira, Urbandale, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 1896 days.

(21) Appl. No.: 10/367,417

(22) Filed: Feb. 13, 2003

(65) Prior Publication Data
US 2003/0221212 A1 Nov. 27, 2003

Related U.S. Application Data

(60) Provisional application No. 60/357,563, filed on Feb. 14, 2002.

(51) Int. Cl.
*A01H 1/00* (2006.01)
*A01H 1/02* (2006.01)
(52) U.S. Cl. ............... 800/275; 800/260; 800/320.1; 800/298
(58) Field of Classification Search .......... 800/260, 800/275
See application file for complete search history.

(56) References Cited

U.S. PATENT DOCUMENTS
5,981,840 A * 11/1999 Zhao et al. ............... 800/294

OTHER PUBLICATIONS
Koester et al. 1993. Crop Sci. 33: 1209-1216.*
Zhao et al. 2001. Molecular Breeding 8: 323-333.*
Koester et al. 1993. Crop Sci. 33: 1209-1216.*

* cited by examiner

*Primary Examiner* — Medina A. Ibrahim
*Assistant Examiner* — Keith O. Robinson
(74) *Attorney, Agent, or Firm* — McKee, Voorhees & Sease, P.L.C.

(57) ABSTRACT

The present invention provides for rapid and large scale evaluation of expression of, or function of, nucleotide sequences in plants. The invention comprises three specific components which provide for fast and large scale evaluation of nucleotide sequences. The first component includes delivery in either a single event a library of different engineered vectors or a single engineered vector for a single target nucleotide sequence comprising sequences the function of which is desired to be known in plant cells. Surprisingly, applicants have discovered that, the introduction of multiple vectors to plant cells predominantly results in individual transgenic plants which contain only a single transformation event. The second feature of the invention involves a highly transformable, fast cycling and/or miniature size plant and the final step involves mass scale analysis of T0 plants for various phenotypes and plasmid rescue to identify the nucleotide sequence present in a particular phenotype.

4 Claims, 2 Drawing Sheets

A

B

METHODS FOR LARGE SCALE FUNCTIONAL EVALUATION OF NUCLEOTIDE SEQUENCES IN PLANTS

CROSS REFERENCE TO RELATED APPLICATIONS

This application claims benefit of the priority date of U.S. Patent Ser. No. 60/357,563 filed Feb. 14, 2002, which is incorporated herein by reference.

BACKGROUND OF THE INVENTION

The recent completion of the genome sequences of a number of bacterial species and several eukaryotes has demonstrated the feasibility and utility of sequencing large genomes. Nucleotide sequencing of the Arapidopsis genome has recently been completed, mapping and sequencing of the rice genome has been nearly completed, and vast quantities of expressed sequence tag information are being obtained from many other plants. This wealth of information provides a powerful tool for application of genetic methods for improving economically important species. However the primary hurdle now is to provide a comprehensive understanding of these sequences and the genetic mechanisms controlling plant growth, development and responses to the environment. The assigning of function to this vast array of sequence information will clearly be the most important and perhaps most time consuming step in plant genomics.

Traditional approaches to assign function to given set of nucleotide sequences such as EST's or various gene/promoter combinations are often not efficient. This is especially true for multi-gene families in which a desired phenotype such as yield, may be determined by only one, or a few of several genes within a gene family. For example in maize the phenotype stalk strength is influenced by the cellulose synthase gene family which can consist of as many as thirty-some sequences in an EST library. Gene knockout methods or transposon tagging are ineffective for multiple gene families and are also time consuming, as it takes approximately four generations and up to three years time before any analysis of function can occur, since rounds of backcrossing and selfing are required to fix a given knockout. Transgene expression for both up and down regulation by transgenics has progressed both in scale and the degree of precision in regulating gene expression. Controlling gene down regulation in transgenic plants has made significant strides with the advent of amplicon, hairpin-loop, and tRNA-like structures which invoke various mechanisms of both transcriptional and Post Transcription Gene Silencing (PTGS) for efficient down regulation. However single gene (vector) transformation using one vector at a time is limited because the analysis of the T0 generation requires follow-up analysis in T1 and subsequent generations. This approach is time consuming when the initial objective is to choose a few candidate sequences for further analysis from among a much larger group of twenty-plus candidate nucleotide sequence combinations. The use of an amplicon-type system in which a virus is used to induce Post Transcription Gene Silencing seems favorable. However, virus induced up and down regulation of expression, particularly for a crop-specific virus system, has only been proven in model species such as *Nicotiana benthaminia*, and expression characteristics are limited by the host viral genome expression characteristics in a given plant species. Thus there is a need in the art for the ability to test a relatively large number of candidate sequences in a parallel system which relies on fast and efficient insertion of nucleotide sequences into expression cassettes, rapid result return from transformation experiments, medium to high throughput analysis, and efficient use of greenhouse and/or growth chamber space to functionally evaluate nucleotide sequences in plants.

It is an object of the present invention to provide a quick and efficient method of mass scale for analysis of nucleotide function in plants.

It is yet another object of the invention to provide vectors which are designed to effect expression of target DNA sequences in plants including up and down regulation of genes for subsequent analysis of its expression products and resulting phenotypes.

It is yet another object of the invention to provide specific protocols to rapidly and efficiently design and construct appropriate expression cassettes and vectors for appropriate constitutive and/or ectopic or not and/or inducible overexpression or post-transcriptional gene silencing of target native or modified cDNAs sequences.

It is yet another object of the invention to provide for use of multiple vectors in a single transformation protocol to generate multiple transformation events, i.e., a "library of vectors" to scale up analysis.

It is yet another object of the invention to provide for in-planta testing by means of a fast cycling plant line to reduce generation time, and maximize greenhouse space to reduce time to analyze phenotypic traits.

It is yet another object to provide high throughput analysis at a phenotypic, biochemical or molecular level to assign function to nucleotide sequences.

SUMMARY OF THE INVENTION

The present invention provides for rapid and large scale evaluation of expression of, or function of, nucleotide sequences in plants. The invention comprises three specific components which provide for fast and large scale evaluation of nucleotide sequences. First, delivery of a library or combination of different engineered vectors (from approximately two (2) to approximately one hundred (100)) which comprise sequences the function of which is disclosed to be known in plant cells. The vectors may be designed to measure effects of a particular gene, sequence or mutation of the same or to determine function of promoter/gene combination in planta. According to the invention this array of vectors is designed to over express, to inhibit via loss of function, or to screen for actuation of multiple sequences in plants. These nucleotide sequences can include plant ESTs, multigene family sequences, different promoter gene combinations as well as sequences designed for up and down regulation of endogenous genes by use of hairpin-loops, tRNA structures and the like.

In a preferred embodiment the vectors are designed to target full length cDNAs and include expression cassettes for consititutive and/or ectopic or not and/or inducible overexpression or post-transcriptional gene silencing of target native or modified cDNAs sequences. These target cDNAs can then be introduced into plants either individually or in batch. Target cDNAs can include any of a number of available libraries such as new libraries which are simultaneously constructed, developmental or tissue specific libraries such as the leaf, tassel, kernel, stem and the like which are known and available to those of skill in the art.

Surprisingly, applicants have discovered that, the introduction of multiple vectors to plant cells (preferably by use of Agrobacterium) predominantly results in individual transgenic plants which contain only a single member of a 'library' of individual sequences incorporated in such libraries. Thus a library composed of a large group of independent vectors can be used with a highly transformable genotype to create a screening event population to determine the function of individual sequences among a group of sequences. Requirements for this analysis include one or more methods of analysis of phenotype, such as biochemical change or molecular change and the ability to identify a specific sequence (vector) which gives rise to the altered phenotype upon review.

The second feature of the invention involves a highly transformable, fast cycling and/or miniature size plant line in which to produce an "event population" used for screening.

The final step involves mass scale analysis of T0 events for various phenotypes and plasmid rescue to identify nucleotide sequence by means known in the art such as PCR using left and right borders into bacteria or direct sequencing.

In a preferred embodiment the identification and plasmid rescue may be accomplished by a U-tag technology.

The method comprises generating a library of unique plasmids that can be stably transformed into a host cell, particularly a plant cell. As described below, the plasmids that constitute the library contain both a U-Tag sequence and a candidate sequence. A U-Tag sequence confers an identifying marker on each plasmid in the library. The U-Tag allows rapid identification and retrieval of plasmids that contain candidate sequences that function in a physiological pathway of interest. The method allows high throughput functional analysis of large numbers of uncharacterized candidate clones in both plant and animal cells.

By "U-Tag" is intended a short, random nucleotide sequence such as an oligonucleotide signature tag (OST) or an intron interrupted signature probe in the untranslated region of a reporter sequence. The U-Tag can be inserted in either the 5' untranslated region or the 3' untranslated region of the reporter sequence. One of skill in the art will recognize that the U-Tag oligonucleotide signature tag can be designed in various ways. The length of the U-Tag can vary depending on the desired complexity of the U-Tag population ranging between about 10-100 nucleotides, about 10-80 nucleotides, about 15-60 nucleotides, or about 15-50 nucleotides.

One method for designing U-Tags allows the development of a population of U-Tags with equivalent melting temperatures among the members of the population and maximizes the differences between the U-Tags to increase specificity during hybridization. The U-Tag population will contain about 30%-70% GC content, about 40%-60% GC content, or about 45%-55% GC content. The U-Tag oligonucleotides can be assembled from blocks of 3 to 6 deoxynucleotides of G, A, T, and C (or a subset thereof) in various combinations, such that each block contains no more than one duplicated nucleotide at any position. Blocks are strung together to generate combinations of blocks. In this way, even a one-block difference between two sequences will always result in a 3 base pair difference between U-Tags. The blocks could be synthesized in two unique sets having an overlapping constant domain that allows them to be ligated to each other in random combination during cloning.

A "hit" clone is a nucleotide sequence of interest that modulates, directly or indirectly, the activity of a transcriptional regulatory region. By "modulates the activity" of a transcriptional regulatory region is intended an increase or decrease in the efficacy or efficiency of a transcriptional regulatory region as measured by a 0.5%, 1%, 5%, 10%, 20%, 30%, 40%, 50%, 60%, 70%, 80%, 90%, or 100% change in transcript levels of a reporter sequence controlled by the transcriptional regulatory region. The reporter sequence includes the U-TAG. Thus, a "hit" clone will be characterized by an alteration in the expression level of the associated U-TAG. In one embodiment, the relative expression levels of each U-TAG with and without a nucleotide sequence of interest in the second DNA construct are compared. In another embodiment, the relative expression of each U-TAG with and without a nucleotide sequence of interest in the first DNA construct are compared.

Identification of the "hit" clones relies on amplification of the U-TAG population from the host cells in a fashion that preserves relative signature abundance sufficient to allow outliers ("hit" clones that modulate the activity of the transcriptional regulatory region) to be selected, either by low abundance, high abundance, or absence of the U-TAG from the signature pool. Any method available in the art can be used to identify "hit" clones. Since the field of high throughput DNA detection and discrimination is growing rapidly, the method of DNA detection and discrimination is not critical to the instant invention. Various methods of detecting and identifying "hit" clones are currently known and any method, which provides for effective DNA detection and discrimination may be employed.

One method for DNA detection employs the use of oligonucleotide arrays in which complementary oligonucleotide signatures used to tag the library are arrayed on a microchip and hybridized with labeled cDNA amplified from the U-TAG region of mRNA transcripts. Such an oligonucleotide array will be referred to herein as a "complementary U-TAG array." Another method for DNA detection is sequencing probe concatamers such as those used in Serial Analysis of Gene Expression (SAGE) (U.S. Pat. No. 5,866,330 herein incorporated by reference). Additional methods include the use of solid-phase capture systems combined with parallel sequencing that allow U-TAGs to be captured, arrayed, and sequenced in large numbers. Another method for DNA detection includes quantitative PCR using primers based on the U-TAG sequences in combination with a detection system that allows amplified product to be detected above a background of non-amplified material. Commercial kits and equipment are available (e.g. Taqman) to one of skill in the art to accomplish semi-quantitative PCR detection of low-level sequences at high throughput (for example, spin blotting used for polymorphism detection and TUSC). Yet another method of DNA detection includes hybridization to colony blots in which the amplified mRNA U-TAG population is hybridized to the original input library DNA in array format (generated by lysis on membranes of replica-plated bacterial colonies on a grid array) under conditions that allow differences in U-TAG frequency to be detected. An additional method is mass spectrometry of amplified probe fragments to distinguish molecular weights and/or fragmentation patterns (e.g. Deforce et al. (2000) *Adv. Chromatogr.* 40:539).

The preparation of probe or sequencing template can be aided by 10-20 rounds of PCR using primers flanking the U-TAG. Conditions are adjusted to minimize any skewing of relative frequencies of individual tags. Once amplification has increased the probe amount to approximately $10^{15}$ copies, linear amplification can be accomplished with T7 DNA polymerase, primed by a T7 promoter included at the 3' end of one of the initial primers.

For sequence based detection methods, much larger U-TAG populations can be used. One method of preparing U-TAG templates for sequencing is as follows. The RT-PCR amplified U-TAG domain contains flanking restriction enzyme sites that, when cleaved, result in self-ligatable ends to form a U-TAG concatamer. Random juxtaposition of appropriate bases at low frequency at these fragment junctions results in reconstitution of a second, internal restriction site that allows cleavage of the concatamers into clonable fragment sizes each of which "reads out" 30 or more U-TAG sequences.

After "hit" U-TAGS are identified, the candidate clone containing the "hit" U-TAG and a nucleotide sequence of interest must be identified and isolated. This can be done through several methods. In one method, the original pool of clones used for expression in the host cell can be arrayed to allow the U-TAG containing "hit" clone to be identified using the U-TAG as a labeled probe. Another method to identify candidate clones is by long-range PCR followed by nested PCR. The U-TAG plus a second primer flanking the candidate nucleotide sequence of interest are used to amplify a larger region containing the entire candidate nucleotide sequence of interest, and then nested primers directly flanking the nucleotide sequence of interest are used to amplify sequenceable DNA.

In methods of identifying and isolating "hit" U-TAGS that comprise hybridization techniques, all or part of a known nucleotide sequence is used as a probe that selectively hybridizes to other corresponding nucleotide sequences present in the library population. By "population" is intended a group or collection. The hybridization probes may be cDNA fragments, genomic DNA fragments, RNA fragments, or other oligonucleotides, and may be labeled with a detectable group such as $^{32}P$ or any other detectable marker. Thus, for example, probes for hybridization can be made by labeling synthetic oligonucleotides based on the non-redundant U-TAG sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.

In methods that are comprised of a PCR approach, methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York) all of which are herein incorporated by reference. Known methods of PCR include, but are not limited to, methods using paired primers, nested primers, single specific primers, degenerate primers, gene-specific primers, vector-specific primers, partially-mismatched primers, and the like.

For purposes of this application the following terms shall have the definitions recited herein. Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5$^{th}$ edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Canteen, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

As used herein, "chromosomal region" includes reference to a length of a chromosome that may be measured by reference to the linear segment of DNA that it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). See also, Creighton (1984) Proteins W. H. Freeman and Company.

By "ectopic", with respect to expression, is meant expression of a DNA sequence in a cell, tissue, organ or at a time where it is not natively expressed. In other words, expression is now spatially and/or temporally modified. By "non-ectopic" or "not ectopic" is meant expression of a DNA sequence in a cell, tissue, organ, where it is natively expressed but now it can be expressed in a modified manner, including, but not limited to, over expression, under expression, or other kinetic changes in expression of said DNA sequence in its native location or time of expression.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17:477-498 (1989)). Thus, the maize preferred codon for a particular amino acid may be derived from known gene sequences from maize. Maize codon usage for 28 genes from maize plants are listed in Table 4 of Murray et al., supra.

As used herein "full-length sequence" in reference to a specified polynucleotide or its encoded protein means having the entire amino acid sequence of, a native (non-synthetic), endogenous, biologically active form of the specified protein. Methods to determine whether a sequence is full-length are well known in the art including such exemplary techniques as northern or western blots, primer extensions, S1 protection, and ribonuclease protection. See, e.g., *Plant Molecular Biology: A Laboratory Manual*, Clark, Ed., Springer-verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNNAUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells, may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, "nucleic acid" or "nucleotide" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, $2^{nd}$ ed., Vol. 1-3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "phenotype" includes the morphology, physiology, biochemistry, or gene expression alterations in any of the above from that of the untransformed plant.

As used herein, the term "plant" can include reference to whole plants, plant parts or organs (e.g., leaves, stems, roots, etc.), plant cells, seeds and progeny of same. Plant cell, as used herein, further includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include modified cells, such as, protoplasts, obtained from the aforementioned tissues. The class of plants which can be used in the methods of the invention is generally as broad as the class of higher plants amenable to transformation techniques, including both monocotyledonous and dicotyledonous plants. Particularly preferred plants include maize, soybean, sunflower, sorghum, canola, wheat, alfalfa, cotton, rice, barley, and millet.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons as "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such as Agrobacterium or Rhizobium. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". The following is a list of tissue preferred or tissue specific promoters.

TABLE A

Exemplary tissue specific or tissue-preferred promoters for use in the performance of the present invention.

| GENE SOURCE | EXPRESSION PATTERN | REFERENCE |
|---|---|---|
| α-amylase (Amy32b) | aleurone | Lanahan, M. B., et al., Plant Cell 4:203-211, 1992; Skriver, K., et al. Proc. Natl. Acad. Sci. (USA) 88:7266-7270 1991 |

TABLE A-continued

Exemplary tissue specific or tissue-preferred promoters for use in the performance of the present invention.

| GENE SOURCE | EXPRESSION PATTERN | REFERENCE |
|---|---|---|
| cathepsin β-like gene | aleurone | Cejudo, F. J., et al. Plant Mol. Biol. 20:849-856 (1992) |
| *Agrobacterium rhizogenes* rolB | cambium | Nilsson et al., Physiol. Plant, 100:456-462 (1997) |
| PRP genes | cell wall | http://salus.medium.edu/mmg/tierney/ntml |
| barley ltr1 promoter | endosperm | |
| synthetic promoter | endosperm | Vicente-Carbajosa et al., Plant J. 13:629-640 (1998) |
| AtPRP4 | flowers | http://salus.medium.edu/mmg/tierney/html |
| chalene synthase (chsA) | flowers | Van der Meer, et al., Plant Mol. Biol. 15:95-109 (1990) |
| LAT52 | anther | Twell et al, Mol. Gen Genet. 217:240-245 (1989) |
| apetala-3 | flowers | |
| chitinase | fruit (berries, grapes, etc.) | Thomas et al. CSIRO Plant Industry, Urrbrae, South Australia, Australia; http://winetitles.com.au/gwrdc/csh95-1.html |
| rbcs-3A | green tissue (eg leaf) | Lam, E. et al., The Plant Cell 2:857-866, 1990; Tucker et al., Plant Physiol. 113:1303-1308 (1992) |
| leaf-specific genes | leaf | Baszczynski, et al., Nucl. Acid Res. 16:4732 (1988) |
| atPRP4 | leaf | http://salus.medium.edu/mmg/tierney/html |
| Pinus cab-6 | leaf | Yamamoto et al., Plant Cell Physiol. 35:773-778 (1994) |
| SAM22 | senescent leaf | Crowell, et al., Plant Mol. Biol. 18:459-466 1992 |
| *R. japonicum* nif gene | nodule | U.S. Pat. No. 4,803,165 |
| *B. japonicum* nifH gene | nodule | U.S. Pat. No. 5,008,194 |
| GmENOD40 | nodule | Yang, et al., The Plant J. 3:573-585 |
| PEP carboxylase (PEPC) | nodule | Pathirana, et al., Plant Mol. Biol. 20:437-450 (1992) |
| leghaemoglobin (Lb) | nodule | Gordon, et al., J. Exp. Bot. 44:1453-1465 (1993) |
| *Tungro bacilliform* virus gene | phloem | Bhattacharyya-Pakrasi, et al, The Plant J. 4:71-79 (1992) |
| sucrose-binding protein gene | plasma membrane | Grimes, et al., The Plant Cell 4:1561-1574 (1992) |
| pollen-specific genes | pollen; microspore | Albani, et al., Plant Mol. Biol. 15:605, 1990; Albani, et al., Plant Mol. Biol. 16:501 (1991) |
| Zm13 | pollen | Guerrero et al., Mol. Gen. Genet. 224:161-168 (1993) |
| apg gene | microspore | Twell et al Sex. Plant Reprod. 6:217-224 (1993) |
| maize pollen-specific gene | pollen | Hamilton, et al., Plant Mol. Biol. 18:211-218 (1992) |
| sunflower pollen-expressed gene | pollwn | Baltz, et al., The Plant J. 2:713-721 (1992) |
| *B. napus* pollen-specific gene | pollen; anther; tapetum | Arnoldo, et al., J. Cell. Biochem. Abstract No Y101, 204 (1992) |
| root-expressible genes | roots | Tingey, et al., EMBO J. 6:1 (1987) |
| tobacco auxin-inducible gene | root tip | Van der Zaal, et al., Plant Mol. Biol. 16:983 (1991) |
| β-tubulin | root | Oppenheimer, et al., Gene 63:87 (1988) |
| tobacco root-specific genes | root | Conkling, et al., Plant Physiol. 93:1203 (1990) |
| *B. napus* G1-3b gene | root | U.S. Pat. No. 5,401,836 |
| SbPRP1 | roots | Suzuki et al., Plant Mol. Biol. 21:109-119 (1993) |
| AtPRP1; AtPRP3 | roots; root hairs | http://salus.medium.edu.mmg/tierney/html |
| RD2 gene | root cortex | http://www2.cnsu.edu/ncsu/research |
| TobRB7 gene | root vasculature | http://www2.cnsu.edu/ncsu/research |
| AtPRP4 | leaves; flowers; lateral root primordia | http://salus.medium.edu/mmg/tierney/html |

TABLE A-continued

Exemplary tissue specific or tissue-preferred promoters for use in the performance of the present invention.

| GENE SOURCE | EXPRESSION PATTERN | REFERENCE |
|---|---|---|
| seed-specific genes | seed | Simon, et al., Plant Mol. Biol. 5:191 (1985); Scofield, et al., J. Biol. Chem. 262:12202 (1987); Baszcynski, et al., Plant Mol. Biol. 14:633 (1990) |
| Brazil Nut albumin | seed | Pearson et al., Plant Mol. Biol. 18:235-245 (1992) |
| legumin | seed | Ellis, et al., Plant Mol. Biol. 10:203-214 (1988) |
| glutelin (rice) | seed | Takaiwa, et al., Mol. Gen. Genet. 208:15-22 (1876); Takaiwa, et al. FEBS Letts. 221:43-47 (1987) |
| zein | seed | Matzke et al., Plant Mol. Biol. 14 (3):323-32 (1990) |
| napA | seed | Stalberg, et al., Planta 199:515-519 (1996) |
| sunflower oleosin | seed (embryo and dryseed) | Cummins, et al., Plant Mol. Biol. 19:873-876 (1992) |
| LEAFY | shoot meristem | Weigel et al., Cell 69:843-859 (1992) |
| *Arabidopsis thaliana* knat1 | shoot meristem | Accession number AJ131822 |
| *Malus domestica* knl | shoot meristem | Accession number Z71981 |
| CLAVATA1 | shoot meristem | Accession number AF049870 |
| stigma-specific genes | stigma | Nasrallah, et al., Proc. Natl. Acad. Sci. USA 85:551 (1988); Trick, et al., Plant Mol. Biol. 15:203 (1990) |
| class 1 patatin gene | tuber | Liu et al., Plant Mol. Biol. 153:386-395 (1991) |
| biz2 | endosperm | EP99106056.7 |
| PCNA rice | meristem | Kosugi et al., Nucleic Acids Research 19:1571-1576 (1991); Kosugi S. and Ohashi Y., Plant Cell 9:1607-1619 (1997) |

A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions, chemical/biochemical challenge or the presence of light. Tissue specific, tissue preferred, cell type specific, and inducible promoters constitute the class of "non-constitutive" promoters. A "constitutive" promoter is a promoter which is active under most environmental conditions.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/ transduction/transposition) such as those occurring without deliberate human intervention.

As used herein, a "expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein") The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and may be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 50° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267-284 (1984): $T_m$=81.5° C.+16.6(log M)+0.41(% GC)−0.61(% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of the complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acids Probes*, Part I, Chapter 2, Ausubel, et al., Eds., Greene Publishing and Wiley-Interscience, New York (1995).

As used herein, the term "structural gene" includes any nucleotide sequence the expression of which is desired in a plant cell. A structural gene can include an entire sequence encoding a protein, or any portion thereof. Examples of structural genes are included hereinafter are intended for illustration and not limitation.

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237-244 (1988); Higgins and Sharp, CABIOS 5:151-153 (1989); Corpet, et al., *Nucleic Acids Research* 16:10881-90 (1988); Huang, et al., *Computer Applications in the Biosciences* 8:155-65 (1992), and Pearson, et al., *Methods in Molecular Biology* 24:307-331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et a., *Nucleic Acids Res.* 25:3389-3402 (1997). Software for performing BLAST analyses is publicly available, e.g., through the National Center for Biotechnology-Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149-163 (1993)) and XNU (Claverie and States, *Comput. Chem.*, 17:191-201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4:11-17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e)(I) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or preferably at least 70%, 80%, 90%, and most preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the imaximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) (ii) The terms "substantial Identity" in the context of a peptide indicates that a peptide comprises a sequence with at least 70% sequence identity to a reference sequence, preferably 80%, or preferably 85%, most preferably at least 90% or 95% sequence identity to the reference sequence over a specified comparison window. Optionally, optimal alignment is conducted using the homology alignment algorithm of Needleman and Wunsch, *J. Mol. Biol.* 48:443 (1970). an indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

DETAILED DESCRIPTION OF THE FIGURES

DETAILED DESCRIPTION OF THE INVENTION

Figure 1:
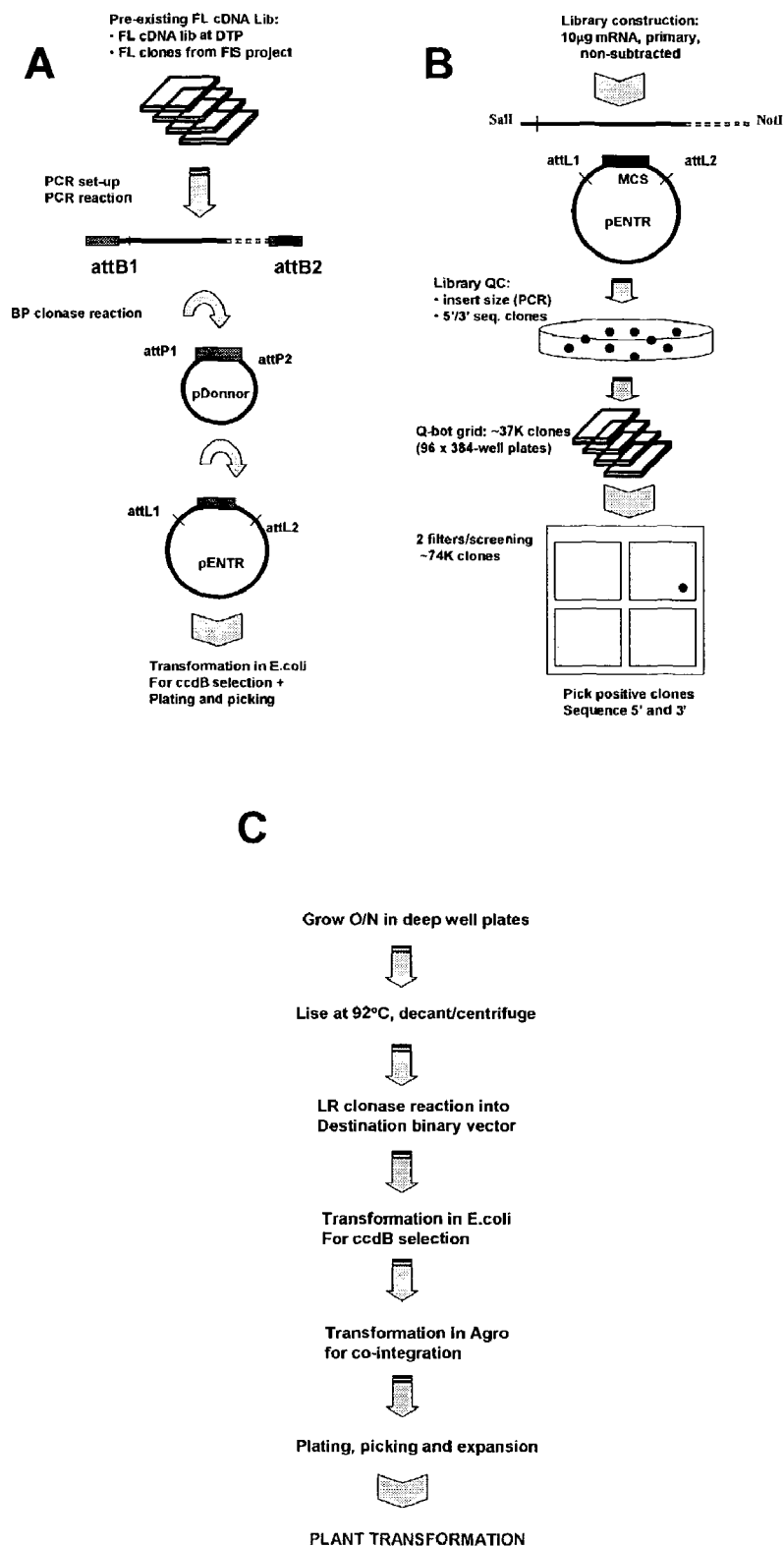
FIGS. 1A and 1B are diagrams depicting one example of a cloning strategy for creating and selecting vectors which may be used according to the invention.
FIG. 1C is an HTP cloning description.

High throughput transformation with model maize genotypes are capable of about 1000 independent events per year per researcher. Approximately 50 different promoter gene combinations can be delivered into corn per year using this technology. The number of candidate genes and promoters ready for testing in corn has increased the requirements for integrative transformation to verify gene expression and/or phenotypic modification by orders of magnitude. Functional gene expression measurement (functional genomics) of 500-1000 promoter/gene combinations per year per person is required to align this phase of evaluation with the other portions of the genomics approach to gene discovery and utilization. The essence of the functional genomics approach is efficient, biologically relevant gene expression in vegetative and seed tissue, including seed, of a plant without the necessity of prolonged evaluation in seed generations. Gene expression is preferably limited to a single plant generation including the vegetative and reproductive tissue of a transgenic plant.

The invention includes the use of vectors preferably Agrobacterium based libaries which make use of various genes or control elements from molecular biology, and also techniques used in molecular biology for library based screening. An event population of transformed plant cells is created and then analyzed for phenotype, biochemical change, or molecular change. Finally, the specific sequence (ie. the vector sequence) which gives rise to an altered phenotype is identified using standard techniques.

The first aspect of the invention comprises the use of multiple vectors, or "vector libraries" of different vectors designed for analysis of function of nucleotide sequences. The vector library typically constitutes a physical mixture of equal quantities of each vector so that each vector has an equal chance to be taken up by each recipient cell. Applicants have surprisingly found that the use of a physical mixture of multiple vectors introduced to cells predominantly result in individual transgenic plants which only contain one of the vectors initially used for transformation. This provides for multiple screening of different vectors for a single transformation procedure and vastly improves efficiency.

Such vector libraries can include a series of promoter/gene combinations aiming at, but not limited to, the up and down regulation of of target cDNAs expression. The component vectors of the library can be designed based on a specific target traits of study or based on a particular gene family the function of which is desired. For example, a "library" or "sub-library" might consist of all the candidate genes that are involved in lignin or cellulose biosynthesis. This would be especially significant in the context of multi-gene families whose individual genic contribution to phenotypes such as stalk strength, brittle snap, or stress response is currently unknown.

In a preferred embodiment a universal vector library can be created by incorporating a special feature in the vectors used for the library such as, for instance, an up- or down-regulation mechanism.

The nucleotide sequences can include native or modified (e.g. mutants, deletions, protein chimeras, domain swaps and the kind) plant ESTs, multigene family sequences, different promoter gene combinations or, preferably, sequences designed for up and down regulation of these genes by use of specific nucleotide modifications such as hairpin-loops, tRNA structures and the like.

For example, in maize, stalk strength is influenced by the cellulose synthase gene family which can consist of as many as thirty-some full length sequences in an EST library. According the invention a library array of vectors comprising as many as 20 or more vectors comprising different cellulose synthase EST fragments can be introduced to plant cells to form the event population. A RNA self pairing loop can be included so that the function of each of these sequences is inhibited and the event population is then screened for phenotypic effects on stalk strength or other beneficial (or detrimental) features.

In a preferred embodiment, the array of vectors are designed to inhibit function of the introduced sequences to identify phenotypic traits associated with a particular EST or gene sequence. Numerous methods of inhibitory or down regulation of nucleotide sequences vectors are known in the art and may be useful for the present invention. For example, PCT publication number WO 99/53050 the disclosure of which is incorporated herein by reference describes means and methods for reducing phenotypic expression of a nucleic acid of interest in cells by introducing to cells a chimeric gene encoding sense and antisense nucleic acid molecules directed towards a target nucleic acid, such that the sense and antisense regions are capable of forming a double stranded RNA region by base pairing between the regions with the sense and antisense sequence. A vector is introduced to the cells which comprises a DNA region which when transcribed yields an RNA molecule with a nucleotide sequence comprising a sense nucleotide sequence, and an antisense nucleotide sequence including at least 10 consecutive nucleotides of the complement of the sense nucleotide sequence so that the RNA is capable of forming an artificial hairpin RNA structure.

Other mechanisms include the Virus Induced Gene Silencing (VIGS) system which can be used to examine gene function in Nicotiana spp. In this system, genes or gene fragments of interest are inserted into a modified Potato Virus X (PVX; potesviral group) cDNA, and RNA transcripts are prepared in vitro for infection of *N. benthamiana* seedlings (Ruiz et. al 1988). Post-transcriptional gene silencing results in less mRNA for endogenously expressing plant genes that have a sequence similarity of approximately 80% or more with the sequences carries by the virus. In addition, cDNAs of only 300-500 bp are sufficient to effect silencing. Thus full length cDNAs or genes are not required. See, The Plant Cell Vol. 12 691-705 May 2000, Burton et. al. "Virus-Induced silencing of a Plant Cellulose Synthase Gene" pg 691-705. A review of other methods for designing nucleic acid vectors for down regulation or inhibition of endogenous genes is Balcombe, (1996) *Plant Cell* 8 1833-1844.

A combination of vectors for, but not limited to, both up and down regulation of the same sequences would be particularly desirable. Thus, the most critical sequences could be determined for a given trait with a single round of transformation using a component library.

In a further embodiment, an example of techniques for designing vectors for full length cDNA clones from existing cDNA libraries or a new full length cDNA library follow, description of sample expression cassettes are described in Example 3.

The first method is PCR based and the target is a cDNA library (FIG. 1a) and/or individual full length cDNA clones. The desired full length ESTs are identified by computer analysis to contain a translation starting codon (e.g. ATG) and a translation stop codon (e.g. TGA) and/or a poly A tail ("native" structure). The clones will be amplified by PCR using primers designed to contain both a overhang homologous recombination site such as FRT sites, lox-cre system or lambda att system (e.g. Gateway system) and a general vector-specific sequence to allow annealing to most plasmids. These systems are commonly used and known in the art. The PCR reaction will be carried out by a high-fidelity proofreading enzyme (Pfx, Tgo or similar). In the example described herein, Example 3, the lambda att recombination system (commercially available as "Gateway" system, Invitrogen Life Technologies, Carlsbad, Calif.) is described. With or without purification, the PCR products generated as described above will be mixed with BP clonase and the plasmid pDONR"x" (containing the ccdB poison gene flanked by attP recombination sites). After the BP recombination reaction the product will be transformed in *E. coli* where the "by product" plasmid containing the ccdB marker will be selected against. Remaining colonies will be picked containing the desired full length clone now flanked by attL sites and ready for recombination with an plasmid compatible with Agrobacterium-based transformation. Yet another procedure to amplify the target sequences is to use primers which contain a general vector-specific sequence to allow annealing to most cDNA-bearing plasmids and sub-clone the subsequent amplification products into another plasmid which contain its multiple cloning sites flanked by attL recombination sites.

Another source of full cDNA clones may come from newly-constructed, homologous recombination-compatible cDNA libraries (e.g. cloned into attL-containing vectors, see FIG. 1B). The libraries can be made from different pools of tissue covering a broad range of plant parts, development and growth cycle using a protocol which has been demonstrated to enrich for full length cDNAs. After construction the libraries will be plated, QCd (insert size and 5'/3' seq of a statistically significant number of clones) and gridded in a Q-bot (e.g. 96×384-well plates=37K clones/library). Each library will then be spotted in Nylon membranes in duplicate for probing. Once there is a desire to express a particular cDNA sequence the following steps will be taken a) a suitable library will be identified "in silico" based on the frequency of the desired cDNA/EST in a given tissue, for example those based on PHI-Dupont EST database, and b) a 5'-end most probe will be designed (e.g. 30 mer oligo end labeling, overhang oligo probes). A pool of probes can be used to probe the filter containing the library of choice, for example, but not limited to, 10-20 probes at a time can be used. Clones can be harvested at random for mini-prep, for example, but not to be limited to, 100-200 clones can be harvested at a time. Deconvolution of clones will be performed by restriction enzyme analysis after agarose gel electrophoresis. Identical restriction patterns will be matched to a single original DNA sequence and one clone will be picked to proceed in the queue. The clone will be 5'/3' sequenced to assure integrity and full length-status. Thereafter the clone will be ready for recombination with an Agro-based JT parent plasmid.

Transformation techniques used will typically be those known in the art and will preferably be inoculation type procedures using Agrobacterium based vectors, such as that used in Burton et al. supra. These are preferred simply due to the speed with which transformation and analysis can occur. The vector is typically introduced to vegetative rather than reproductive cells. Some potential DNA delivery and/or inoculation procedures which could be used according to the invention include: direct inoculation of vector DNA or Agrobacterium by syringe into young seedlings, direct inoculation of vector DNA or Agrobacterium into young vegetative leaves by portable biolistic device (Biorad), DNA delivery into dry seeds of vector DNA or Agrobacterium using sonication to facilitate penetration of DNA into internal vegetative tissue, DNA delivery into 'imbibition' stage of vector DNA or Agrobacterium by precise timing of treatment of corn seeds. DNA delivery of vector DNA or Agrobacterium aided by sonication of imbibition stage seeds, DNA delivery of vector DNA or Agrobacterium into early germinating seeds or immature embryos of corn either directly or aided by sonication. Gene expression for these protocols is facilitated by incorporation of viral genes in the vector for cell to cell movements or propagation of signal molecules throughout vegetative tissue. Of course standard delivery techniques may also be used according to the invention and are intended to be within the scope of the same as described herein.

The recipient cells from which the event population is generated are also an important feature of the preferred embodiment. The recipient cells are preferably from a fast cycling, highly transformable and/or dwarf variety of a particular plant species. Typical of these for maize would be any of the publically available Gaspe Bay flint line of varieties. Most preferable are F1 hybrids of Gaspe bay Flint X QTM (Quick Turnaround Maize, a publically available form of Gaspe bay Flint modified for growth under greenhouse conditions). Resultant transgenic plants are reduced in size such that growth space is reduced to a 4' pot (¼ space of normally sized maize plant), and mature in less that 2.5 months. (Traditionally 3.5 months are required to obtain transgenic T1 seed once transgenic plants are acclimated to the greenhouse). Another such line is disclosed in PCT publication WO 99/12411. It discloses the generation of miniature plants, Micro-Tom and Micro-peach, which are characterized by reduced size, maturation to produce viable seeds or tubers at a plant density of at least 10-fold higher than standard growth conditions for a commercial plant of the same species, and capable of being crossed with a commercial plant of the same species. Methods for generating these types of plants are also disclosed. These sorts of varieties exist for almost every plant species and are known or capable of being generated by those of skill in the art.

Transformation is preformed on immature embryos of the highly transformable genotype using the 'library' mixture of Agrobacterium with sufficient numbers to produce an 'event population' which can be used for screening. Analysis of seed generation is not included.

The event population (typically this will be T0) is then analyzed for phenotype. High throughput analysis at the phenotypic (eg. height, maturity, seed set), biochemical (eg. herbicide resistance) or molecular level (direct analysis of gene expression of marker or other genes incorporated into vector sequences) is next performed to identify those plants which are relevant to the trait of interest. For example, plants may be visually screened for differences in stalk strength, and those plants that evidence improved (or reduced) strength will be selected. Further, of course, any plant which evidences any change may also be selected, even if not associated with the particular trait of interest.

Finally, the selected plants are analyzed using standard molecular techniques, to ascertain which vector was present. These techniques include but are not limited to Southern blot, Rt-PCR and are disclosed in Maniatis et al, Molecular Cloning: A Lab Manual (Cold Spring Harbour Press.)

Knowing the function of various nucleotide sequences in plants provides researches with the tools for the generation of transgenic plants with improved agronomic traits. This can include the introduction of beneficial structural genes or the inhibition of others, the possibilities are endless. For example the optimum gene from the cellulose synthase family which has a desired effect on stalk lodging may be identified by the methods of invention and used to generate transgenic plants with improved stalk strength. Further, the identification of function of nucleotide sequences also provides information that can be used to produce various essential plant proteins on a large scale basis through bacterial production of recombinant proteins and the like.

Transgenic Techniques Overview

According to the present invention, nucleotide sequences are expressed in transformed plants. Production of genetically modified plant tissue either expressing or inhibiting expression of a nucleotide sequence combines the teachings of the present disclosure with a variety of techniques and expedients known in the art. In most instances, alternate expedients exist for each stage of the overall process. The choice of expedients depends on the variables such as the plasmid vector system chosen for the cloning and introduction of the recombinant DNA molecule, the plant species to be modified, the particular nucleotide sequence ie. structural gene, promoter elements and upstream elements, design of up or down regulation elements, used. Persons skilled in the art are able to select and use appropriate alternatives to achieve functionality. Culture conditions for expressing desired nucleotide sequences and cultured cells are known in the art. Also as known in the art, a number of both monocotyledonous and dicotyledonous plant species are transformable and regenerable such that whole plants containing and expressing desired genes under regulatory control of the promoter molecules according to the invention may be obtained. As is known to those of skill in the art, expression in transformed plants may be tissue specific and/or specific to certain developmental stages. Truncated promoter selection and structural gene selection are other parameters which may be optimized to achieve desired plant expression or inhibition as is known to those of skill in the art and taught herein.

The following is a non-limiting general overview of Molecular biology techniques which may be used in performing the methods of the invention.

Structural Gene

In one embodiment, the nucleotide sequence may be a structural gene, the function of which is desired to be known in a particular plant, or tissue type. Thus be means of the present invention, agronomic genes can be expressed in transformed plants to identify function of the same, temporally or spatially or with a certain promoter combination. Examples of structural genes, the function of which in plant cells may be assayed include:

Plant disease resistance genes, (Martin et al., Science 262: 1432 (1993) (tomato Pto gene for resistance to *Pseudomonas syringae* pv. tomato encodes a protein kinase); a *Bacillus thuringiensis* protein, (Geiser et al., Gene 48: 109 (1986); a lectin, (Van Damme et al., Plant Molec. Biol. 24: 25 (1994)); a vitamin-binding protein, (such as avidin. see PCT application US93/06487); an enzyme inhibitor, (Abe et al., J. Biol. Chem. 262: 16793 (1987)); an insect-specific hormone or pheromone, (see, for example, Hammock et al., Nature 344: 458 (1990)); an insect-specific peptide or neuropeptide, (Regan, J. Biol. Chem. 269: 9 (1994)); an insect-specific venom, (Pang et al., Gene 116: 165 (1992); an enzyme responsible for an hyperaccumulation of a monterpene; an enzyme involved in the modification, including the post-translational modification, of a biologically active molecule; for example, a glycolytic enzyme, a proteolytic enzyme; (See PCT application WO 93/02197); a molecule that stimulates signal transduction, (for example, Botella et al., Plant Molec. Biol. 24: 757 (1994)); a transcriptional activator (see for example Lotan et al., Cell 93:1195-1205 (1998) Arabidopsis LEAFY COTYLEDON 1 is sufficient to induce embryo development in vegetative cells) a hydrophobic moment peptide, (PCT application WO95/16776); a membrane permease, (Jaynes et al., Plant Sci. 89: 43 (1993)); a viral-invasive protein or a complex toxin derived therefrom, (Beachy et al., Ann. Rev. Phytopathol. 28: 451 (1990)); (Taylor et al., Abstract #497, SEVENTH INT'L SYMPOSIUM ON MOLECULAR PLANT-MICROBE INTERACTIONS (Edinburgh, Scotland, 1994)); a virus-specific antibody, (Tavladoraki et al., Nature 366: 469 (1993)); a developmental-arrestive protein produced in nature by a pathogen or a parasite, (Lamb et al., Bio/Technology 10: 1436 (1992)); a developmental-arrestive protein produced in nature by a plant, (Logemann et al., Bio/Technology 10: 305 (1992)); a herbicide that inhibits the growing point or meristem, such as an imidazalinone or a sulfonylurea, (Lee et al., EMBO J. 7: 1241 (1988)); Glyphosate (resistance imparted by mutant 5-enolpyruvl-3-phosphikimate synthase (EPSP) and aroA genes, respectively) (U.S. Pat. No. 4,940,835); a herbicide that inhibits photosynthesis, such as a triazine (psbA and gs+ genes) and a benzonitrile (nitrilase gene). (Przibilla et al., Plant Cell 3: 169 (1991)); Modified fatty acid metabolism, for example, by transforming a plant with an antisense gene of stearoyl-ACP desaturase to increase stearic acid content of the plant. See Knultzon et al., Proc. Natl. Acad. Sci. USA 89: 2624 (1992); decreased phytate content, (Van Hartingsveldt et al., Gene 127: 87 (1993)); modified carbohydrate composition, for example, by transforming plants with a gene coding for an enzyme that alters the branching pattern of starch. (See Shiroza et al., J. Bacteriol. 170: 810 (1988)); genes that controls cell proliferation and growth of the embryo and/or endosperm such as cell cycle regulators (Bogre L et al., "Regulation of cell division and the cytoskeleton by mitogen-activated protein kinases in higher plants." Results Probl Cell Differ 27:95-117 (2000).

Exemplary genes implicated in this regard include, but are not limited to, those categorized below.

Promoters

The promoters disclosed herein may be used in conjunction with naturally occurring flanking coding or transcribed sequences of the desired structural gene/s or with any other coding or transcribed sequence that is critical to structural gene formation and/or function.

It may also be desirable to include some intron sequences in the promoter constructs since the inclusion of intron sequences in the coding region may result in enhanced expression and specificity. Thus, it may be advantageous to join the DNA sequences to be expressed to a promoter sequence that contains the first intron and exon sequences of a polypeptide which is unique to cells/tissues of a plant critical to seed specific Structural formation and/or function.

Additionally, regions of one promoter may be joined to regions from a different promoter in order to obtain the desired promoter activity resulting in a chimeric promoter. Synthetic promoters which regulate gene expression may also be used.

The expression system may be further optimized by employing supplemental elements such as transcription terminators and/or enhancer elements.

Other Regulatory Elements

In addition to a promoter sequence, an expression cassette or construct should also contain a transcription termination region downstream of the structural gene to provide for efficient termination. The termination region or polyadenylation signal may be obtained from the same gene as the promoter sequence or may be obtained from different genes. Polyadenylation sequences include, but are not limited to the Agrobacterium octopine synthase signal (Gielen et al., *EMBO J.* (1984) 3:835-846) or the nopaline synthase signal (Depicker et al., *Mol. and Appl. Genet.* (1982) 1:561-573).

Marker Genes

Recombinant DNA molecules containing any of the DNA sequences and promoters described herein may additionally contain selection marker genes which encode a selection gene product which confer on a plant cell resistance to a chemical agent or physiological stress, or confers a distinguishable phenotypic characteristic to the cells such that plant cells transformed with the recombinant DNA molecule may be easily selected using a selective agent. One such selection marker gene is neomycin phosphotransferase (NPT II) which confers resistance to kanamycin and the antibiotic G-418. Cells transformed with this selection marker gene may be selected for by assaying for the presence in vitro of phosphorylation of kanamycin using techniques described in the literature or by testing for the presence of the mRNA coding for the NPT II gene by Northern blot analysis in RNA from the tissue of the transformed plant. Polymerase chain reactions are also used to identify the presence of a transgene or expression using reverse transcriptase PCR amplification to monitor expression and PCR on genomic DNA. Other commonly used selection markers include the ampicillin resistance gene, the tetracycline resistance and the hygromycin resistance gene. Transformed plant cells thus selected can be induced to differentiate into plant structures which will eventually yield whole plants. It is to be understood that a selection marker gene may also be native to a plant.

Transformation

A recombinant DNA molecule whether designed to inhibit expression or to provide for expression containing any of the DNA sequences and/or promoters described herein may be integrated into the genome of a plant by first introducing a recombinant DNA molecule into a plant cell by any one of a variety of known methods. Preferably the recombinant DNA molecule(s) are inserted into a suitable vector and the vector is used to introduce the recombinant DNA molecule into a plant cell.

The use of Cauliflower Mosaic Virus (CaMV) (Howell, S. H., et al, 1980, *Science*, 208:1265) and gemini viruses (Goodman, R. M., 1981, *J. Gen Virol.* 54:9) as vectors has been suggested but by far the greatest reported successes have been with *Agrobacteria* sp. (Horsch, R. B., et al, 1985, *Science* 227:1229-1231).

Methods for the use of Agrobacterium based transformation systems have now been described for many different species. Generally strains of bacteria are used that harbor modified versions of the naturally occurring Ti plasmid such that DNA is transferred to the host plant without the subsequent formation of tumors. These methods involve the insertion within the borders of the Ti plasmid the DNA to be inserted into the plant genome linked to a selection marker gene to facilitate selection of transformed cells. Bacteria and plant tissues are cultured together to allow transfer of foreign DNA into plant cells then transformed plants are regenerated on selection media. Any number of different organs and tissues can serve as targets from Agrobacterium mediated transformation as described specifically for members of the Brassicaceae. These include thin cell layers (Charest, P. J., et al, 1988, *Theor. Appl. Genet.* 75:438-444), hypocotyls (De-Block, M., et al, 1989, *Plant Physiol.* 91:694-701), leaf discs (Feldman, K. A., and Marks, M. D., 1986, *Plant Sci.* 47:63-69), stems (Fry J., et al, 1987, *Plant Cell Repts.* 6:321-325), cotyledons (Moloney M. M., et al, 1989, *Plant Cell Repts.* 8:238-242) and embryoids (Neuhaus, G., et al, 1987, *Theor. Appl. Genet.* 75:30-36), or even whole plants using in vacuum infiltration and floral dip or floral spraying transformation procedures available in *Arabidopsis* and *Medicago* at present but likely applicable to other plants in the hear future. It is understood, however, that it may be desirable in some crops to choose a different tissue or method of transformation.

Other methods that have been employed for introducing recombinant molecules into plant cells involve mechanical means such as direct DNA uptake, liposomes, electroporation (Guerche, P. et al, 1987, *Plant Science* 52:111-116) and micro-injection (Neuhaus, G., et al, 1987, *Theor. Appl. Genet.* 75:30-36). The possibility of using microprojectiles and a gun or other device to force small metal particles coated with DNA into cells has also received considerable attention (Klein, T. M. et al., 1987, *Nature* 327:70-73).

In accordance with the invention, it is not necessary for the vector to be expressed or integrated to reproductive cells of the plant. In fact it is preferred that vegetative cells be the recipient of the vector and transient transformants used for the event population to screen for phenotypes in the fastest amount of time.

The regenerated plants are transferred to standard soil conditions and cultivated in a conventional manner.

Following transformation of target tissues, expression of the above-described selectable marker genes allows for preferential selection of transformed cells, tissues and/or plants, using regeneration and selection methods now well known in the art.

The foregoing methods for transformation would typically be used for producing a transgenic variety. The transgenic variety could then be crossed, with another (non-transformed or transformed) variety, in order to produce a new transgenic variety. Alternatively, a genetic trait which has been engineered into a particular maize line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

The following examples serve to better illustrate the invention described herein and are not intended to limit the invention in any way. All references cited herein are hereby expressly incorporated to this document in their entirety by reference.

EXAMPLES

Example 1

Transformation with Multiple Gene Expression Vectors for Functional Genomics Study Immediate Experimental Objectives:
To test the concept of transformation with multiple gene vector or a defined gene expression library:
1. Transformation simultaneously with multiple vectors using a model maize genotype to produce a large population (number) of transgenic events for gene expression analysis.
2. Analyze the transgenic population using molecular and phenotypic tools to test how the gene expression vectors are represented in the transgenic event population, and particularly to test whether all the gene expression vectors are equally or near-equally represented in the transgenic event population.
3. Analyze the transgene profile in transgenic events to see whether each of the majority of transgenic events represents a particular transgene.
Transformation Method:
Maize transformation experiments were performed using a standardized, high-efficiency Agrobacterium-mediated transformation protocol.
Transformation Experimental Designs:
1. Agrobacterium Gene Expression Vectors Used for Initial Experiment:
PHP10525 containing the Ubi::GUS marker gene
  PHO15033 containing the UBI-GFP marker gene
  PHP14276 containing the Act1-GAI gene (Expression of the GAI gene will result in shorter plant phenotype)
  PHP15068 containing the 35S-PVX amplicon which will give special visible symptom such as leaf necrosis and early senescence.
2. Preparation of Agrobacterium Culture:
Culture Agrobacterium with each vector separately on solid medium plates. Prepare Agrobacterium cell suspension in liquid medium for each vector separately using culture from the solid medium plates. Adjust the concentration of Agrobacterium cells in the suspension (measured by OD) to the same concentration for all Agrobacterium vectors. Mix equal amounts of Agrobacterium cell suspension culture of each vector to make a mixture in which the Agrobacterium cell concentration for each vector is the same.
3. Treatment of Maize Immature Embryos Agrobacterium Culture and Generation of Transgenic Plants:
Treat immature maize embryos with the premixed Agrobacterium cell culture (vector mixture), select transformed callus events and regenerate transgenic plants using the standardized transformation protocol.
For the initial experiments, treat 200-300 maize embryos from GS3 or a GS3xinbred cross, generate ~100 callus events (transformation efficiency was in the range of 40-50%), regenerate at least 2 T0 plants from each callus event and send ~100 events/200 T0 plants to the greenhouse for molecular and phenotypic analyses.
Analysis of Transgenic T0 Plants
Analyze all T0 events (including both T0 plants derived from the same individual transgenic callus event) to determine the distribution of the four different component vectors within the transgenic event population. Specific analysis examples follow.
1. GUS Assay with Leaf Tissue of T0 Plants
Perform GUS staining for all T0 events, record results, and see whether GUS-positive events count for ~25% of all the transgenic events.
2. GFP expression Observation in T0 Plants
Observe GFP expression in non-green tissue such as root, leaf base or leaf vein of young T0 plants, record results and see whether GFP-expression events count for ~25% of all transgenic events.
3. PCR Analysis of all T0 Plants
Sample all T0 plants and perform PCR analysis for all four transgenes, GUS, GFP, GAI, and PVX amplicon. Record results and see whether the percentage of events containing each of the four transgenes.
Results from the PCR analysis will allow us to establish the transgene profile in T0 plants with regards to the four gene constructs used for transformation.
4. Phenotypic Evaluation of T0 Transgenic Plants
Measure T0 plant height to see how many (what percentage) plants show significant height reduction, compare with PCR results for the GAI gene to see correlation between height reduction phenotype and the existence of the GAI gene.
Observe leave necrosis/leaf senescence in T0 plants, record results, and compare with PCR results for the PVX amplicon sequence to see correlation between necrosis phenotype and the existence of the PVX amplicon sequence.
5. Southern Blot Analysis of Transgenic Plants
Collect samples from T0 plants for Southern blot analysis. The necessity and the importance of the Southern results will depend on how results from the above analyses are correlated in order to interpret the data.
Results and Conclusion:
In our initial transformation experiments more than 150 resistant callus events were generated. One hundred-twenty resistant calli were transferred to regeneration medium for plant regeneration. T0 plants from 92 events were sent to the greenhouse for molecular analysis and phenotypic evaluation. All 92 events were sampled for PCR analysis for all four potential transgenes on the four respective vectors used for transformation. Based on PCR analysis results and reliable phenotype evaluation, all four vectors are nearly equally represented in the transgenic event population, indicating that the probability for each vector to be transformed into maize cells is nearly equal (see Table 1). This does not exclude the possibility that a particular transgene may have a positive or negation effect on its own transformation and subsequent recovery of transgenic events and regeneration of transgenic plants. About 85% of the transgenic events contain only one of the four transgenes and only 15% of the transgenic events contain two or three transgenes (see Table 2). Out of the 92 transgenic events, none of them contains all four transgenes used for transformation. The PCR results only indicate the presence/absence of a particular transgene in transgenic plants and do not provide information on copy number of each transgene.

From these preliminary results we come to the conclusion that multiple Agrobacterium vectors or a pre-defined library of Agrobacterium vectors can be simultaneously transformed into maize plant cells and allow to generate a transgenic event population that will equally or nearly equally represent all vectors. Furthermore, the majority (more than 85%) of the transgenic events contain only one transgene; this makes it possible to easily link the presence of a particular transgene to a particular transgene phenotype. We are planning an experiment to use this approach for testing a group of candidate genes for a target trait.

TABLE 1

Transgene distribution in transgenic event population

| Total Event# | GUS+ | GFP+ | GAI+ | Amplicon+ |
|---|---|---|---|---|
| 92 | 37 | 23 | 22 | 26 |
| 100% | 40.2% | 25% | 23.9% | 28.3% |

TABLE 2

Transgene profiles in individual transgenic events

| Transgene Profile | Event # | % |
|---|---|---|
| 1 transgene | 78 | 84.8% |
| 2 transgenes | 12 | 13.0% |
| 3 transgenes | 2 | 2.2% |
| 4 transgenes | 0 | 0.0% |
| Total transgenic event # | 92 | 100% |

Example 2

Gaspe Flint Hybrid Maize Transformation and Transgenic Evaluation

Our initial experimental objective was to evaluate and establish an efficient transformation system for Gaspe Flint (GF) maize or a cross with GF maize. The small ear size of Gaspe Flint produces very limited number of embryos for transformation. However, Gaspe Flint is a very good pollen producer. Cross GS3 or A188 ears with Gaspe Flint pollen produced ears with excellent seedset that are as good as GS3 or A188 ears from selfing or sibling pollination. Thus, immature embryos from crosses of GS3xGaspe Flint and A188xGaspe Flint were used as Agrobacterium transformation target tissue in our initial transformation experiments.

F1 embryos were transformed with Agrobacterium-mediated transformation method using standard protocols established for GS3 and A188. Two Agrobacterium vectors, PHP10525 (35S::BAR//Ubi::GUS) and PHP10626 (35S::BAR//Ubi::GFP), were used in these initial transformation experiments. The transgenic nature of selected callus events was first confirmed by GUS assay or by live GFP observation. Transformation efficiency based on callus event number after 9-10 weeks selection are: 9% for A188XGF, 33% for GS3XGF.

Plants were regenerated from selected GS3XGF callus events and sent to the greenhouse for further gene expression analysis. The growth/development characters as well as maturity and fertility of transgenic plants were also evaluated. Transgenic GS3XGaspe Flint plants grown in the greenhouse became ready for pollination in 4-5 weeks after being transplanted into soil and produced mature seeds in 75 days. Thus, the GS3XGaspe Flint F1 plants still maintain their early maturity character.

Both regular size pots (8") and small-size pots (4") were used to grown GS3XGF transgenic plants. The transgenic plants grown, develop, and yield equally well in both regular pots and small pots. Thus, growing the small-size transgenic plants in small pots will significantly save greenhouse space. On the per plant basis, one Gaspe Flint maize plant will use only 20-30% of the space that is used for a regular inbred or hybrid maize plant.

T1 seeds were harvested from GS3XGF transgenic plants and the seedset from these transgenic plants are very good as shown in the following table. More than 50% of the transgenic plants produced more 100 kernels and more than 90% of the transgenic plants produced more 20 kernels.

| Gene Construct | Total # Transgenic Plants | # of Plants with >20 Kernels | % >20 Kernels | # of Plants with >100 Kernels | % >100 Kernels |
|---|---|---|---|---|---|
| 10525 | 45 | 42 | 93 | 23 | 51 |
| 10626 | 31 | 28 | 90 | 20 | 65 |

GS3XGF transgenic events with kernel-specific promoter::GUS constructs (PHP15425: ZAG2.1::gus and PHP15422: ZAG2.4::gus) were also generated and sent to the greenhouse for evaluation. T1 kernel development was normal compared to other maize inbreds or hybrid used for transformation. Transgene expression pattern in develop kernels of GS3XGaspe Flint transgenic was also evaluated in comparison with that of regular corn hybrids or inbreds and there is no difference found.

Screening for transformability and tissue culture response of the BC1 embryos (GS3XGFXGF) was completed. Responsive embryos with highly embryogenic type II callus were selected for plant regeneration. Through continuous backcrossing and screening for transformability and preferred tissue culture characteristics we expect to recover new, highly transformable Gaspe Flint maize lines. These new maize lines should be an ideal model genotype for transformation and provide a useful tool for functional genomics study.

In yet another experiment, 12 different gene constructs were mixed together for Agrobacterium-mediated transformation. These gene constructs were selected based on available assays (such as GUS, GFP CRC), tissue specificity of promoter (constitutive, embryo-specific, endosperm-specific, anther-specific, stalk-preferred), and predicted phenotype (stature change, male sterility, herbicide resistance). The mixed gene constructs were transformed into F1 embryo of GS3xGaspe Flint, a potential model system for future gene evaluation and discovery. 160 T0 events were produced and sent to the greenhouse, with each independent event represented by a single T0 plant.

All T0 plants were sampled for PCR analysis for the presence of each of 12 different transgenes. T0 plants in the greenhouse were evaluated phenotypically at different stage (plant height, tassel branch number, fertility/sterility, resistance to herbicide Dormax conferred by one moCAH construct. Marker gene expression in predicted target tissues were also assayed. Seeds were harvested from all T0 plants that were able to produce ear and set seed. Stalk tissues were also harvested from the T0 plants.

Major Conclusions Form Preliminary Data Analysis:

1. Equal representation of vector members: Based on PCR analysis data, the majority of the gene constructs are represented in the transgenic event population with the predicted percentage or close to that percentage. Out of the 12 gene constructs, a couple of constructs were over-represented and 1 construct was under-represented, suggesting that the transgene expression from these constructs may have positive or negation effects on transformation or tissue culture proliferation. The GS3 X GaspeBay genotype was used to evaluate a defined library approach to validating gene function among a set of 12 genes whose phenotypic expression has been previously characterized. Of interest, two constructs were over represented Ubi:Abi4 (77 out of 160 events where 12 would be expected with random assortment) and Glb1:gfp and one construct was under represented (ubi:rice GE) with only 2 events out 160 total events. Expression pattern and plant phenotypic expression are identical to traditional genotypes such as GS3 X HC69. Single transgenes were observed in 60% of the individual plants (events).

2. Reflection of same promoter tissue specificity observed in normal maze genotype: In general, constitutive or tissue-specific gene expression in GS3xGaspe reflect what have been previously observed in normal maize genotypes such as GS3, HG11, HC69. For example, Glb1 promoter also regulated embryo-specific expression in >10 DAP seed; GZ (Gamma zein) promoter regulates endosperm-specific expression.

3. Express same or similar phenotypes from transgene: Expression of transgene with previously known phenotype also produced exactly the same phenotypes in GS3xGaspe T0 plants. For example, MS 5126 promoter regulates anther-specific expression of the DAM gene, leading to male sterility in almost all PCR-positive plants; Stalk-preferred expression of the D8mpl gene regulated by the S2A promoter also gave dwarf phenotype in GS3xGaspe T0 plant; Expression of rice GE gene produced the same long-leaf phenotype in T0 plants.

4. Based on incomplete PCR analysis of transgene profile in each transgenic event, ~60% of the events contained only one transgene.

Example 3

High Efficiency Generation of Expression Cassettes for Targeted Gene Approach

Figure 2:
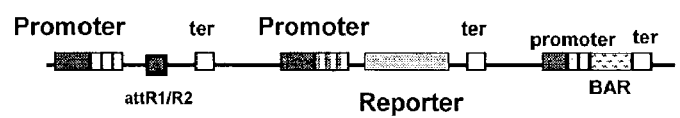
FIGS. 2A and 2B are maps showing the expression cassettes in FIG. 1 that may be used according to the invention.
Figure 2:
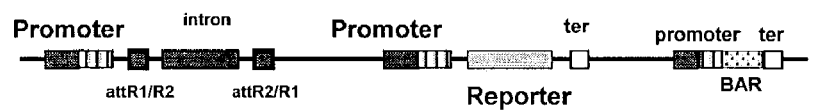

1) Plasmid/cassette for overexpression of FL cDNA (Vector A): The desired native cDNA (5' UTR->polyA) is flanked by homologous recombination sites such as FRT recombination sites, lox-cre recombination sites or lambda att recombination sites (e.g. Gateway system). In the example described below the lambda att recombination system (commercially available as "Gateway" system, Invitrogen Life Technologies, Carlsbad, Calif.) is described in more detail. The FL cDNA containing the attL sites will be inserted into the attR sites in Agro-based binary vector by recombination (FIG. 2). These attR sites will be flanked by a promoter of choice at its 5' and a pinII termination site at its 3'. In addition, this expression vector may contain a reporter gene (e.g. GUS, YFP, CFP, etc.) flanked by a promoter of choice at its 5' and a pinII termination site at its 3' (for T0 expression monitoring and T1 segregation analysis). The BAR resistant marker will be driven either by Ubi or 35S promoters. The promoters themselves in this construct can be flanked by recombination sites or its modifications to facilitate the exchange of this regulatory elements between different plasmids.

2) Plasmid/cassette for downregulation (post-transcriptional gene silence, PTGS) of FL cDNA (Vector B): The desired native cDNA (5' UTR->polyA) is flanked by homologous recombination sites such as FRT recombination sites, lox-cre recombination sites or lambda att recombination sites (e.g. Gateway system). In the example described herein the lambda att recombination system (commercially available as "Gateway" system, Invitrogen Life Technologies, Carlsbad, Calif.) is described in more detail. The native cDNA (5' UTR->polyA) flanked by the attL sites will be recombined into two inverted attR sites flanking an intron (e.g. Adh1) in the Agrobacterium binary vector (FIG. 2). This attR1/R2::Adh1 intron::attR2/R1 cassette will be flanked by a promoter of choice at its 5'. In addition, this expression vector may contain a reporter gene flanked by a promoter of choice at its 5' and a pinII termination site at its 3' (for T0 expression monitoring and T1 segregation analysis). The BAR resistant marker will be drive either by Ubi or 35S promoters. The promoters themselves in this construct can be flanked by recombination sites or its modifications to facilitate the exchange of this regulatory elements between different plasmids.

HTP Cloning Description (FIG. 1c):

The bacterial clone containing the desired FL cDNA (attL) will be grown O/N in deep well plates and submitted to lyses at 92-95° C. After decantation/centrifugation, a sample of the culture's supernatant will be mixed with a purified DNA stock of the expression plasmid DNA (attR) and RL clonase. Following incubation the products will be transformed into E. coli for ccdB-driven negative selection of byproduct plasmids. One isolated colony will be electroporated into LB4404 Agrobacterium for co-integration. After selection and QC one clone will be selected for further expansion and transformation.

Transformation, screening and selection of transformed plants based upon phenotype is conducted as described earlier herein.

What is claimed is:

1. A method for making a fast cycle time maize line with a high rate of transformation efficiency for screening transgenes comprising:
   a) crossing a plant from a Gaspe Flint line with a second maize plant from a GS3(HiII) or A188 line having a high rate of transformation efficiency;
   b) producing inbred progeny from said cross; and
   c) selecting inbred progeny that are of miniature plant size capable of being grown in a four inch pot, have a cycle time of less than 2½ months in combination with a high rate of transformation efficiency, thereby producing progeny for screening transgenes.

2. The method of claim 1 wherein the fast cycle time maize line has a transformation efficiency of 9% or greater.

3. The method of claim 1 wherein the fast cycle time maize line has a transformation efficiency of 33% or greater.

4. The method of claim 1 wherein producing inbred progeny comprises backcrossing.

* * * * *